US011337613B2

(12) United States Patent
Xu (10) Patent No.: US 11,337,613 B2
(45) Date of Patent: May 24, 2022

(54) BED

(71) Applicant: Xinqiang Xu, Shenzhen (CN)

(72) Inventor: Xinqiang Xu, Shenzhen (CN)

( * ) Notice: Subject to any disclaimer, the term of this patent is extended or adjusted under 35 U.S.C. 154(b) by 149 days.

(21) Appl. No.: 16/572,173

(22) Filed: Sep. 16, 2019

(65) Prior Publication Data

US 2020/0093379 A1  Mar. 26, 2020

(30) Foreign Application Priority Data

Sep. 20, 2018 (CN) .......................... 201811103125.1
Sep. 20, 2018 (CN) .......................... 201821542321.4
Mar. 12, 2019 (CN) .......................... 201920307561.4

(51) Int. Cl.
*A61B 5/0205* (2006.01)
*A61G 7/05* (2006.01)
*A61B 5/00* (2006.01)
*A61B 5/024* (2006.01)

(52) U.S. Cl.
CPC .......... *A61B 5/0205* (2013.01); *A61B 5/0002* (2013.01); *A61B 5/02444* (2013.01); *A61B 5/742* (2013.01); *A61G 7/0527* (2016.11); *A61B 5/6891* (2013.01)

(58) Field of Classification Search
CPC ... A61B 5/0205; A61B 5/0527; A61B 5/0002; A61B 5/02444; A61B 5/742; A61B 5/6891
See application file for complete search history.

(56) References Cited

U.S. PATENT DOCUMENTS 6,679,830 B2 * 1/2004 Kolarovic ............. A61G 11/00
                                                          600/22
2014/0266733 A1 * 9/2014 Hayes ................. A61B 5/0205
                                                          340/573.4

(Continued)

FOREIGN PATENT DOCUMENTS

| CN | 105193393 A | 12/2015 |
| CN | 108095444 A | 6/2018 |
| JP | 2001070256 A | 3/2001 |

(Continued)

OTHER PUBLICATIONS

European Search Report dated Nov. 18, 2019 tor corresponding European application No. EP 19 19 8296 pp. 1-9.

(Continued)

*Primary Examiner* — Michael W Kahelin
*Assistant Examiner* — Naveed R. Kolia
(74) *Attorney, Agent, or Firm* — Intellectual Property Law Group LLP (57) ABSTRACT

A bed includes: a bed body having a space for a user to rest; a monitoring device connected to the bed body, the monitoring device including a pressure detecting mechanism, a signal processing unit electrically coupled to the pressure detecting mechanism, and a monitoring unit electrically coupled to the signal processing unit. The pressure detecting mechanism is configured to detect pressure variations of the bed body, generate pressure data, and transmit the pressure data to the signal processing unit. The signal processing unit is configured to process the pressure data and generate processed signal data. The monitoring unit is configured to monitor the processed signal data.

18 Claims, 5 Drawing Sheets

(56) References Cited

U.S. PATENT DOCUMENTS

2014/0352060 A1* 12/2014 Hirose ................. A61G 7/0527
5/310
2016/0183695 A1* 6/2016 Veron .................... A47D 15/00
340/573.1

FOREIGN PATENT DOCUMENTS

| JP | 2009022565 A | 2/2009 |
| JP | 2014-2333488 A | 12/2014 |
| JP | 2017153743 A | 9/2017 |
| WO | WO 2013108502 A1 | 7/2013 |

OTHER PUBLICATIONS

Japan Office Action dated Sep. 1, 2020 for corresponding Japanese application No. 2019-170096 with English translation, pp. 1-5.
Japan Office Action dated Mar. 9, 2021 for corresponding Japanese application No. 2019-170096 with English translation pp. 1-6.

* cited by examiner

BED

CROSS REFERENCE TO RELATED APPLICATIONS

This application claims priorities under 35 U.S.C. § 119 to Chinese Patent Application No. 2019203075614, filed on Mar. 12, 2019, Chinese Patent Application No. 2018111031251, filed on Sep. 20, 2018, and Chinese Patent Application No. 2018215423214, filed on Sep. 20, 2018, the entire contents of which are incorporated herein in their entireties.

TECHNICAL FIELD

The present disclosure relates to furniture, and more particularly relates to a bed.

BACKGROUND

With the improvement of people's living standards, the demand for health and safety is getting higher and higher. Therefore, a bed, which mainly provides a place for people to rest, can no longer meet functional needs of consumers. A conventional bed has a single function. When a user is at rest, other people cannot know whether the user is in a safe and healthy state or not. If a caregiver wants to know a rest condition of the user, an external measuring device is required for measurement, which make it lack of timeliness.

SUMMARY

According to various embodiments of the present disclosure, a bed is provided.

A bed includes a bed body having a space for a user to rest, and a monitoring device connected to the bed body and including a pressure detecting mechanism, a signal processing unit electrically coupled to the pressure detecting mechanism, and a monitoring unit electrically coupled to the signal processing unit. The pressure detecting mechanism is used to detect pressure variations of the bed body, generate pressure data, and transmit the pressure data to the signal processing unit. The signal processing unit is used to process the pressure data and generate processed signal data. The monitoring unit is used to monitor the processed signal data.

Details of one or more embodiments of the disclosure are set forth in the accompanying drawings and description below. Other features, objects, and advantages of the disclosure will be apparent from the description and appended claims.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only some embodiments of the present disclosure, and persons of ordinary skill in the art can derive other drawings from the accompanying drawings without creative efforts.

DETAILED DESCRIPTION OF THE EMBODIMENTS

In order to make the above objects, features, and advantages of the present disclosure more apparent, specific embodiments of the present application will be described in detail with reference to the accompanying drawings. Numerous specific details are set forth in the description below in order to provide a thorough understanding of the application. However, the present application can be implemented in many other ways than those described herein, and those skilled in the art can make similar modifications without departing from the scope of the present application, and thus the present application is not limited by the specific embodiments disclosed below.

It will be understood that when an element is referred to as being "disposed" or "provided" on another element, it can be directly on the other element or intervening elements may be present. When an element is referred to as being "connected" or "coupled" to another element, it can be directly connected or electrically coupled to another element or intervening elements may be present. The terms "vertical", "horizontal", "left", "right", and the like, as used herein, are for illustrative purposes only and are not intended to be limited as the only embodiment.

Unless otherwise defined, all terms (including technical and scientific terms) used herein have the same meaning as commonly understood by one of ordinary skill in the art to which this disclosure belongs. The terms used in the specification of the present application are only for the purpose of describing specific embodiments, and not to limit the present application.

A conventional bed has a relatively simple function, which can only provide a user with a space for rest and cannot detect a weight of the user. In addition, when a user (e.g., an infant, a patient, or an old person) rests in bed, if the mouth and nose of the user is covered by a foreign substance; or due to imperfect development of the user's own organs; alternatively, when the user is young, ill, or old, these conditions can easily cause safety problems, thereby affecting the safety and health of the user. If a caregiver wants to know a resting condition of the user, an external measuring device is required to detect the user, which makes it lack of timeliness.

Figure 1:
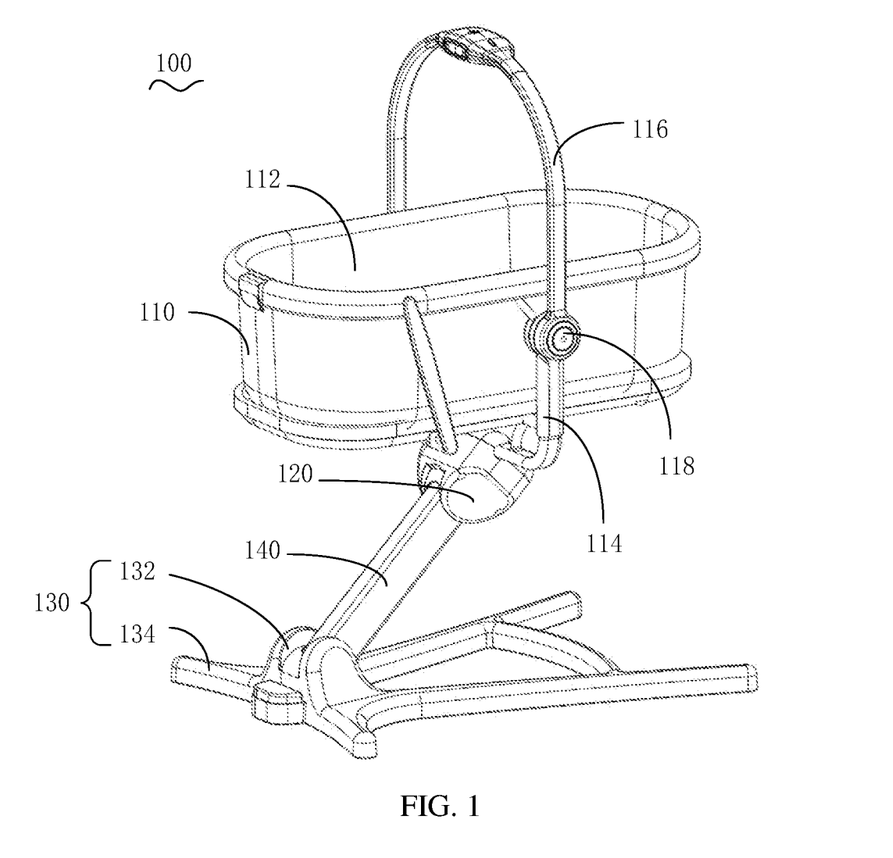
FIG. 1 is a perspective view of a bed in accordance with an embodiment.

Referring to FIG. 1, according to an embodiment, a bed 100 is provided including a bed body 110, a monitoring device 120 connected to the bed body 110, and a bed base 130 connected to the bed body 110.

The bed body 110 has a space 112 for the user to rest. The bed body 110 may be of be a rectangular shape, a cylindrical shape, or an elliptical cylindrical shape.

In some embodiments, the bed body 110 includes a supporting frame 114 and a supporting arm 140. The supporting frame 114 is connected to the bed base 130 via a supporting arm 140. The supporting frame 114 is disposed outside the space 112. The supporting arm 140 is rotatably connected to the supporting frame 114, so that a position of the bed body 110 can be adjusted. The supporting arm 140 is connected to the bed base 130. The bed body 110 may further include a holding frame 116. The supporting frame 114 and the holding frame 116 can be connected to the same connecting portion 118 outside the space 112. The holding frame 116 facilitates a caregiver to carry the bed 100. A pendant, a music player or the like can be provided on the holding frame 116. Both the supporting frame 114 and the holding frame 116 are rotatably connected to the connecting portion 118.

The monitoring device 120 is connected to the bed body 110. The number of the monitoring device 120 can be one or more. The monitoring device 120 can be mounted at various positions of the bed 100. The following examples illustrate examples of the mounting position of the monitoring device 120. It can be understood that the mounting position of the monitoring device 120 is not limited thereto.

In the illustrated embodiment, the monitoring device 120 is disposed at a connection between the supporting frame 114 and the supporting arm 140. It can be understood that the monitoring device 120 can be attached to the connection between the supporting frame 114 and the supporting arm 140, or can be acted as an intermediate connecting member between the supporting frame 114 and the supporting arm 140.

In another embodiment, the monitoring device 120 is disposed on the supporting frame 114. For example, the monitoring device 120 can be disposed on a portion of the supporting frame 114 located below the space 112, or can be disposed on the supporting frame 114 away from the supporting arm 140. The specific position of the monitoring device 120 on the supporting frame 114 is not limited thereto.

In yet another embodiment, the monitoring device 120 is disposed on the bed base 130. For example, the monitoring device 120 can be disposed at a position of the bed base 130 adjacent to the supporting arm 140, or can be disposed at a position of the bed base 130 away from the supporting arm 140, and the like. The specific position of the monitoring device 120 on the bed base 130 is not limited thereto.

In still another embodiment, the monitoring device 120 is disposed on the supporting arm 140. For example, the monitoring device 120 can be disposed at a position of the supporting arm 140 adjacent to the supporting frame 114, or can be disposed at a position of the supporting arm 140 adjacent to the bed base 130, and the like. A specific position of the monitoring device 120 on the supporting arm 140 is not limited thereto.

Figure 2:
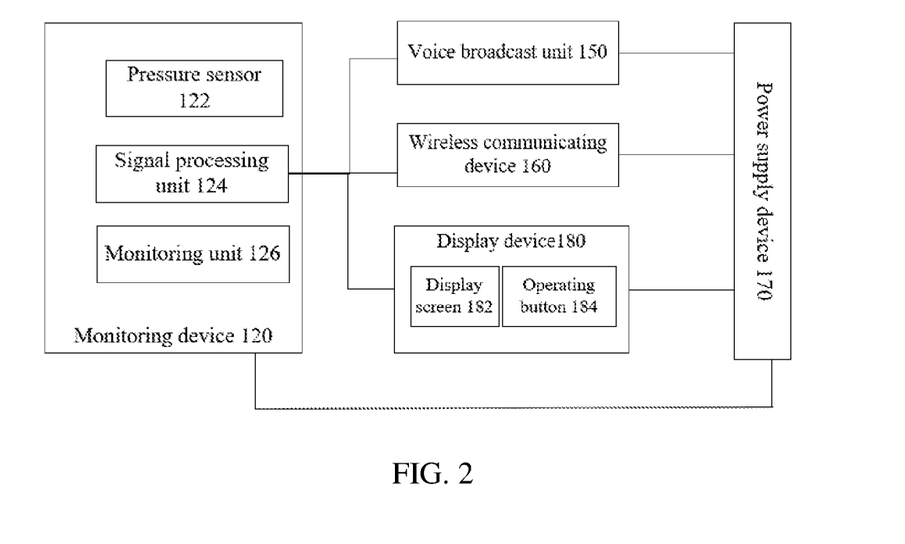
FIG. 2 is a block diagram of the bed of FIG. 1.

Referring to FIG. 2, the monitoring device 120 includes a pressure detecting mechanism 122, a signal processing unit 124 electrically coupled to the pressure detecting mechanism 122, and a monitoring unit 126 electrically coupled to the signal processing unit 124. The pressure detecting mechanism 122 is used to detect pressure variations of the bed body 110, generate pressure variation data, and transmit the pressure variation data to the signal processing unit 124. The signal processing unit 124 is used to process the pressure variation data and generate processed signal data. The monitoring unit 126 is used to receive the processed signal data and monitor the processed signal data.

In this embodiment, the pressure detecting mechanism 122 is connected to the bed body 110. The pressure detecting mechanism 122 is used to detect the pressure variation data of the bed body 110 and transmit the pressure variation data to the signal processing unit 124. The pressure detecting mechanism 122 can detect a pressure difference between the bed body 110 in a loaded state and a unloaded state, and transmit the pressure difference to the signal processing unit 124. The signal processing unit 124 is used to process the pressure difference to generate weight data of the user. The pressure detecting mechanism 122 can also detect the pressure variation data of the bed body 110 during the rest of the user, and transmit a detected pressure variation data to the signal processing unit 124. The signal processing unit 124 is used to process the pressure variation data to sense a rest condition of the user (for example, a breathing condition, a heartbeat condition, and a physical condition of the user during the rest).

The pressure detecting mechanism 122 includes at least one pressure sensor. When the pressure detecting mechanism 122 includes a plurality of pressure sensors, the plurality of pressure sensors can be set to be connected in series or in parallel according to actual requirements. In some embodiments, the pressure detecting mechanism 122 includes only one pressure sensor. The only one pressure sensor can more accurately detect the pressure variations caused by rest actions of the user due to a more concentrated stress point, and avoid an error caused by non-uniform and unstable force exerted by the plurality of pressure sensors.

In some embodiments, the pressure sensor can be a strain-type pressure sensor or a piezoelectric type pressure sensor with a high sensitivity. The strain-type pressure sensor enables a change in pressure generated by a user during rest to be converted into a change in resistance. The piezoelectric pressure sensor enables a change in pressure generated by a user during rest to be converted into a change in voltage. Specifically, the pressure sensor may be a high-precision pressure sensor manufactured by OMRON, Schneider, etc., to realize electromechanical conversion.

It should be understood that pressure sensors having other operating principles can also be employed, such as ceramic pressure sensors, diffused silicon pressure sensors, sapphire pressure sensors, and the like, as long as it can convert the pressure signal generated by the user during rest into some kind of electric signal.

The signal processing unit 124 is used to receive the pressure variation data detected by the pressure detecting mechanism 122, process the pressure variation data, generate processed signal data, and transmit the processed signal data to the monitoring unit 126. The signal processing unit 124 can be a single chip micro controller or a chip capable of data processing. A signal connection established between the signal processing unit 124 and other mechanisms, devices, sensors, or units in the present application can be electrical connection and/or a wireless connection. For example, data can be transmitted between the pressure detecting mechanism 122 and the signal processing unit 124 via wired (electrical connection) or wireless transmission (wireless connection). The wireless connection can be a connection established through wireless communication technologies such as Wi-Fi, Bluetooth, ZigBee, Zwave, WLAN, GSM, 2G, 3G, 4G, and 5G. In this way, the signal processing unit forms a wireless LAN system with other mechanisms, devices, and units, and can perform wireless data or signals transmission.

The monitoring unit 126 is used to receive the processed signal data generated by the signal processing unit 124 and monitor the processed signal data. The signal processing unit 124 and the monitoring unit 126 can be electrically coupled to each other via a wired communication unit or a wireless communication unit to perform data interaction. The wired communication unit is a metal wiring. The wireless communication unit includes at least one of a Wi-Fi module, a Bluetooth module, a ZigBee module one, a Zwave module, a WLAN module, a GSM module, a 2G module, a 3G module, a 4G module and a 5G module.

The monitoring unit 126 can be directly mounted to the bed body 110, or can be attached to other objects, such as a wall, a table, or other household articles, or can be installed in a mobile terminal, a server, or the like.

The breathing, heartbeat, and body movements of the user during rest can cause changes in pressure. In some embodiments, the pressure detecting mechanism 122 is used to detect the pressure variation data generated by the bed body 110 during a user's rest and transmit the pressure variation data to the signal processing unit 124. The signal processing unit 124 is used to process the pressure variation data to sense the breathing condition, the heartbeat condition, and the body condition of the user during the rest, thereby perceiving the rest condition of the user. The body movement can be a movement of the fingers, the head, the legs and feet, etc. of the user. When the pressure of the bed body 110 caused by the aforementioned movements exceeds a preset pressure value. For example, if the breathing is abnormally short or paused, or the heartbeat is abnormally short or paused, or the user's body is greatly shaken or flipped, the monitoring unit 126 can detect a hazard signal and performs an alarm to draw attention of the caregiver. The caregiver can take timely ambulance measure to prevent hazardous situations. In this way, the caregiver can monitor the user's rest condition in time and in real time to improve safety.

Specifically, the user lies in the space 112 defined by the bed body 110, and the pressure variations generated by the user during the rest is transmitted to the pressure detecting mechanism 122. The pressure detecting mechanism 122 is used to detect the pressure variation data and convert the pressure variation data into an electric signal such as a resistance, a voltage, or an inductance. The pressure variation data detected by the pressure detecting mechanism 122 is transmitted to the signal processing unit 124 via wired or wireless transmission. The signal processing unit 124 is used to process the pressure variation data to generate processed signal data, and transmit the processed signal data to the monitoring unit 126 via a wired communication unit or a wireless communication unit.

During the rest of the user, if the pressure data of the bed body detected by the pressure detecting mechanism 122 fluctuates substantially uniformly, it indicates that the rest condition of the user is stable and the user is in a safe condition. The signal processing unit 124 is used to process the pressure variation data detected by the pressure detecting mechanism 122, and transmit a safety signal to the monitoring unit 126 via a wired communication unit or a wireless communication unit. At this time, the monitoring unit 126 is used to monitor the safety signal and collect the processed signal data. During the rest of the user, if the pressure data of the bed body 110 detected by the pressure detecting mechanism 122 does not change or fluctuates abnormally, it indicates that the rest condition of the user is unstable, such as apnea, cardiac arrest, abnormal physical movement, etc., and the user is in a hazardous condition. The signal processing unit 124 is used to process the pressure variation data detected by the pressure detecting mechanism 122, and transmit a hazard signal to the monitoring unit 126 through a wired communication unit or a wireless communication unit. At this time, the detection unit 126 is used to monitor the hazard signal, collect the processed signal data, and give an alarm to draw the attention of the caregiver. In this way, the caregiver can take timely measure to prevent adverse consequences.

It can be understood that the signal processing unit 124 and the monitoring unit 126 can each preset a data range in advance, and if the data is within the preset data range, the monitoring unit merely collects the data; if the data is abnormal, the monitoring unit collects the data and sends an alarm. Changes in breathing, heartbeat, and physical condition produced by the user during the rest are collected and collated by the monitoring unit 126. During the rest of the user, the user can be in a sleep condition, an awake condition, a sitting condition or a lying condition.

In some embodiments, the monitoring unit 126 can receive a safety signal and a hazard signal using a controller to determine whether to alarm. The monitoring unit 126 can be attached to the bed 100 or other objects. In some embodiments, the monitoring unit 126 can alarm by displaying data through a display, by issuing an alert sound through a speaker, or by flashing a warning light to draw attention of the caregiver. This allows the caregivers to find problems and take action in a timely manner. Of course, other alarm modes can be adopted, for example, generating large-amplitude vibration or emitting harmless smoke, etc. The monitoring unit 126 can further include a single-chip microcomputer, a processor, or a chip that can implement data processing, etc., to collect and process the data, record the breathing condition, the heartbeat condition, and the physical condition of the user during the rest, and form a rest record, which can be provided to the caregiver for reference.

In addition, the monitoring unit 126 can be a processor or a cloud server for data processing, and the processor can be installed in the bed 100, or a mobile terminal such as a mobile phone or a tablet. The monitoring unit 126 is used to process the data transmitted by the signal processing unit 124 to form a record or convert the data into a rest parameter, and a reminder or a suggestion can be made according to the rest parameter.

The monitoring device 120 can be directly or indirectly connected to the bed base 130.

The bed base 130 includes a mounting portion 132, and a plurality of legs 134 connected to the mounting portion 132. The supporting arm 140 is rotatably connected to the mounting portion 132. Specifically, the plurality of legs 134 can be directly laid on the ground, which are all connected to the mounting portion 132. Alternatively, the plurality of legs 134 can be placed on the ground and included angles can be defined between the plurality of legs 134 and the ground. All of the legs 134 are connected to the mounting portion 132. The supporting arm 140 is rotatably connected to the mounting portion 132, and an angle between the supporting arm 140 and the bed base 130 can be adjusted, so that a positional relationship, such as a height relationship and a level relationship, between the bed base 130 and the bed body 110 can be adjusted by the supporting arm 140. An angular relationship between the supporting arm 140 and the bed base 130 can be adjusted according to a height and sitting posture of the caregiver. For example, if the height of the caregiver is relatively high, the angle between the supporting arm 140 and the bed base 130 can be increased (0 degrees to 90 degrees), and if the height is relatively short, the angle between the supporting arm 140 and the bed base 130 can be reduced. At this time, the supporting arm 140 and the supporting frame 114 are also rotatably connected, and when the angle between the supporting arm 140 and the bed base 130 is changed, the angle between the supporting arm 140 and the supporting frame 114 is changed as well.

Further, a rotating wheel with a self-locking function can be mounted below the leg 134. The rotating wheel facilitates the movement of the bed 100, and at the same time, the bed 100 can be locked in a proper position to improve safety.

In other embodiments, the bed 100 further includes an voice broadcast unit 150, such as a speaker. The voice broadcast unit 150 is electrically coupled to the signal processing unit 124, and is used to perform voice broadcast on the weight data transmitted from the signal processing unit 124 and detected according to the pressure difference of the bed body 110 in the unloaded state and in the loaded state detected by the pressure detecting mechanism 122.

In other embodiments, the bed 100 further includes a wireless communication device 160. The wireless communication device 160 includes at least one of a Wi-Fi device, a Bluetooth device, a ZigBee device, a Zwave device, a WLAN device, a GSM device, a 2G device, a 3G device, a 4G device, and a 5G device. The wireless communication device 160 performs data interaction between the signal processing unit and a mobile device or a server via a wireless network. The wireless communication device 160 is electrically coupled to the signal processing unit 124, and is used to transmit the weight data, which is obtained by the signal processing unit 124 processing the pressure difference of the bed body 110 in the unloaded state and in the loaded state detected by the pressure detecting mechanism 122, and the breath condition, heartbeat condition, and physical condition data of the user during the rest obtained by the signal processing unit 124 processing the pressure variation data during the rest of the user detected by the pressure detecting mechanism 122 to an external mobile device or a server (mobile device such as a mobile phone) via a wireless network. The mobile device or the server can store the weight data and the breathing condition, heartbeat condition, and physical condition data during the rest of the user, or display the weight data and the breathing condition, heartbeat condition, and the physical condition data during the rest of the user through a certain manner (such as a graph, etc.).

In some embodiments, the bed 100 can further include a power supply device 170 for powering the monitoring device 120. The power supply device 170 can be a disposable battery or a rechargeable battery. It can be understood that the power supply device 170 can also supply power to components that require to be powered after an external alternating current is converted into a direct current.

In some embodiment, the bed 100 further includes a display device 180. The display device 180 is detachably provided on the bed body 110, so that it can be provided at any position of the bed body 110 or at any position in the user's home. The caregiver can place the display device 180 at any convenient location for viewing as needed. The display device 180 is electrically coupled to the signal processing unit 124, and is used to receive and display the data transmitted from the signal processing unit 124. The display device 180 can be electrically coupled to the signal processing unit 124 via a wired or a wireless connection or the like. In this embodiment, the display device 180 and the signal processing unit 124 are wirelessly coupled. The display device 180 includes a display screen 182. The display screen 182 can be a liquid crystal display. The display device 180 can display the user's weight, and can further display the data monitored by the pressure detecting mechanism 122 and the change graph at all times so as to know the rest condition of the user in time. In addition, the display device 180 can be of a touch type or a button type, a preset value can be input in advance, and data of different time periods can be queried.

In some embodiments, the display screen 182 is provided with operation buttons 184 on both sides. The operation button 184 can be at least one of a lock button, an voice broadcast button, a wireless transmission button, a power button, and a clear button. The lock button is used to prevent a display value of the weight from frequently changing due to shaking of the user when the signal processing unit 124 processes the pressure difference of the bed body 110 in the unloaded state and in the loaded state detected by the pressure detecting mechanism 122. When the user presses the lock button, the display value of the weight is no longer changed. The voice broadcast button is used to provide a choice for the user about whether broadcasting the measuring weight thereof in voice or not. When the voice broadcast button is pressed, the voice broadcast unit broadcasts the measuring results, otherwise the broadcasting is not performed. The wireless transmission button is used to provide a choice for the user about whether transmitting the measuring results (e.g. the weight data and the breathing condition, the heartbeat condition, and the physical condition of the user during the rest) to the mobile device or the server via the wireless network. When the wireless transmission button is pressed, the wireless transmission device transmits the measuring results to the mobile device or the server, otherwise the transmission of the measuring results is not performed. The power button is used to supply power the components of bed body 110 required to be powered (such as the monitoring device 120, the display device, the wireless communication device, the voice broadcast device, etc.). When the power button is pressed, the components of bed body 110 required to be powered are powered on, otherwise no power is supplied. In one of the embodiments, a cushion-like article can be placed in the bed body 110 for the comfort of the user. At this time, when the signal processing unit 124 processes the pressure difference of the bed body in a loaded state and in a unloaded state detected by the pressure detecting mechanism 122 to obtain the weight, and the detected weight may be inaccurate due to the presence of the cushion-like article. The clear button is used to eliminate an effect of the cushion-like article on the detected weight. When the clear button is pressed, the detected weight no longer contains the weight of the cushion-like article.

In the aforementioned embodiment, the bed 100 is provided with the monitoring device 120. The pressure detecting mechanism 122 converts the pressure signal of the bed body 110 generated by the user during the rest into an electrical signal, thereby sensing the rest condition of the user. The data detected by the pressure detecting mechanism 122 is transmitted to the signal processing unit 124 over a wired or wireless manner. A processed data processed by the signal processing unit 124 is transmitted to the monitoring device 126 over a wired or wireless manner to perform data interaction. If the processed data is within a normal preset range, the data will be collected. If the processed data is abnormal, the alarm will be performed to cause the attention of the caregiver, and the ambulance measure can be taken in time to prevent the hazardous situation. Therefore, the user's rest condition can be monitored in a timely and real-time manner, and the safety of the user can be improved.

Figure 3:
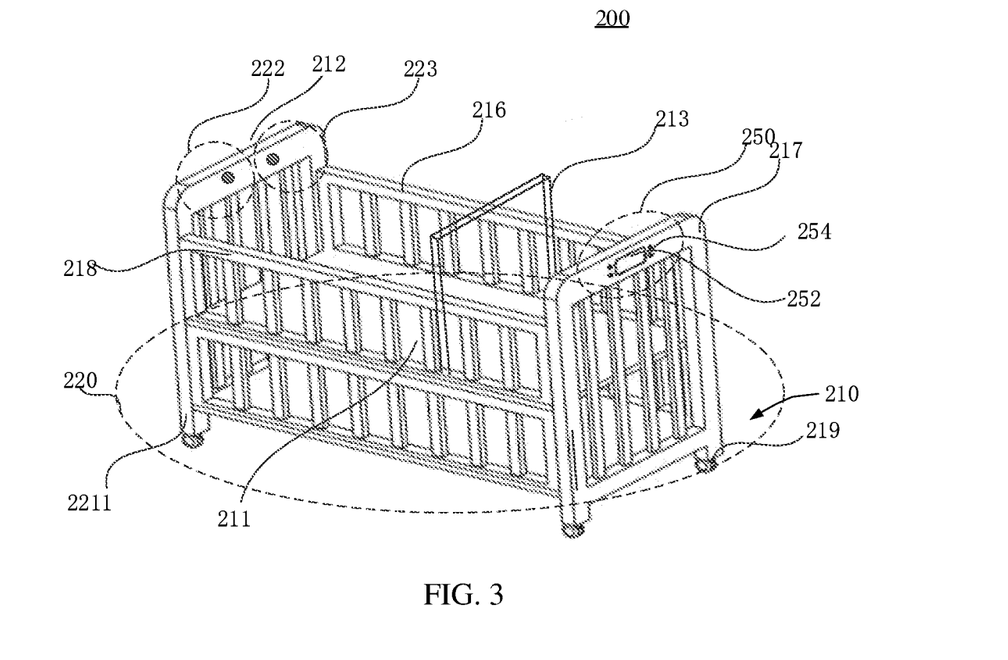
FIG. 3 is a perspective view of a bed in accordance with another embodiment.

Refer to FIG. 3, in another embodiment, a bed 200 is provided, including a bed body 210, a monitoring device 220, and a display device 250. It can be understood that the bed 200 includes, but is not limited to, a baby cot.

The bed body 210 has a space for a user to rest. The bed body 210 may have a substantially rectangular shape, a cylindrical shape, or an elliptical columnar shape. In this embodiment, the bed body 210 has a substantially rectangular shape, and includes a bed plate 211, and a first baffle plate 212, a first side plate 216, a second side plate 217, and a third side plate 218. The first baffle plate 212, the first side plate 216, the second side plate 217, and the third side plate 218 are successively connected and are arranged perpendicularly to the bed plate 211. In this embodiment, the first baffle plate 212 is parallel to the second side plate 217. The first baffle plate 212 is used to abut against a first portion of the user. The first side plate 216 and the third side plate 218 are parallel to each other and are vertically connected to the first and second side plates 212 and 217, respectively. The bed plate 211, the first baffle plate 212, the first side plate 216, the second side plate 217, and the third side plate 218 are enclosed to define the space for the user to rest. The first baffle plate 212, the first side plate 216, the second edition plate 217, and the third side plate 218 can prevent the user (e.g., an infant) from rollover or dropping so as to protect the user. In this embodiment, the bed body 210 further includes a second baffle plate 213 connected to the first side plate 216 and the third side plate 218, respectively. The second baffle plate 213 is located between the first baffle plate 212 and the second side plate 217. A distance between the second baffle plate 213 and the first baffle plate 212 can be adjusted. In one embodiment, the second baffle plate 213 or the first baffle plate 212 can be slidably disposed on the bed plate 211, so as to adjust the distance between the second baffle plate 213 and the first baffle plate 212. The second baffle plate 213 is used to abut against a second portion of the user. In this embodiment, one of the first portion and the second portion is the top head of the user and the other is the sole of the user. It can be understood that the second baffle plate 213 can be without being connected to the first side plate 216 and the third side plate 218, and can be an object provided by the user which can reflect signals, such as a mobile phone, a plastic plate, etc.

In an embodiment, the bed body 210 can further include a plurality of pulleys 219 for moving the bed body 210. A braking device (not shown) can also be provided on the pulleys 219. The caregiver can stop the bed body 210 by pushing the braking device to stop the pulley from moving.

Figure 4:
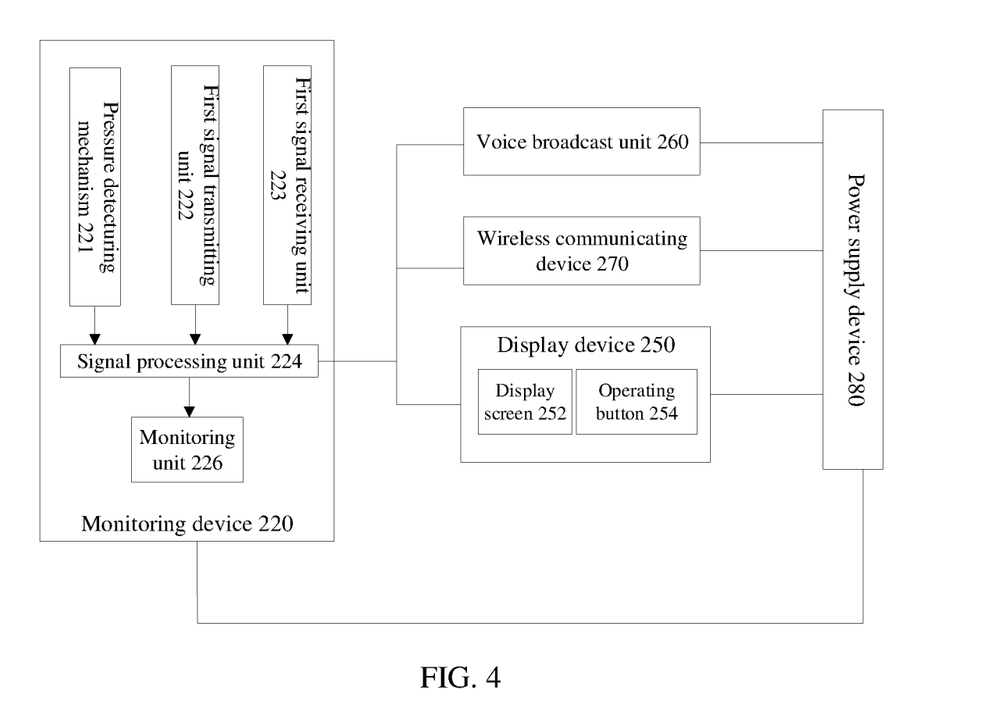
FIG. 4 is a block diagram of the bed of FIG. 3.

Referring to FIG. 4, the monitoring device 220 is disposed on the bed body 210, and includes a pressure detecting mechanism 221, a first signal emitting unit 222, a first signal receiving unit 223, a signal processing unit 224, and a monitoring unit 226.

In some embodiments, the pressure detecting mechanism 221 includes a supporting leg 2211 and a pressure sensor disposed at the supporting leg 2211. The supporting leg 2211 is located below the bed body 210 for supporting the bed body 210. The pressure sensor is used to detect pressure data of the bed body 210. Specifically, the pressure sensor is used to detect a pressure difference of the bed body 210 in a loaded state and in an unloaded state, and pressure variation data of the bed body 210 during rest by the user.

Figure 5:
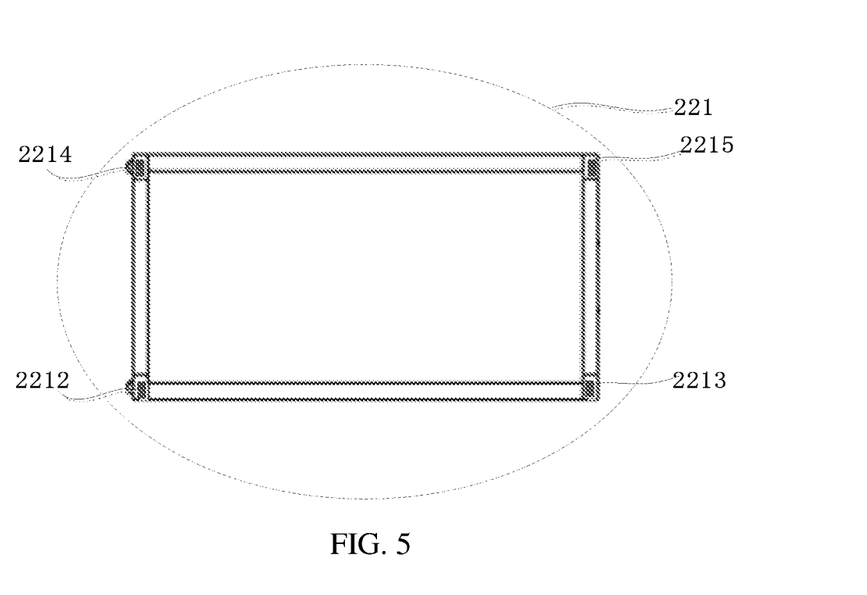
FIG. 5 is a bottom view of a pressure detecting mechanism of FIG. 3.

Referring to FIG. 3, FIG. 4 and FIG. 5, in this embodiment, the pressure detecting mechanism 221 is a four-leg pressure detecting mechanism. The four-leg pressure detecting mechanism is located below the bed body 210 and includes four supporting legs 2211 for supporting the bed body 210. Each supporting leg 2211 is provided with a pressure sensor. Specifically, the four-leg pressure detecting mechanism 221 includes a first sensor 2212, a second sensor 2213, a third sensor 2214, and a fourth sensor 2215 electrically with the signal processing unit 224. The first sensor 2212, the second sensor 2213, the third sensor 2214, and the fourth sensor 2215 cooperatively detect the pressure difference of the bed body 210 in the loaded state and in the unloaded state, and the pressure variation data of the bed body 210 during the rest of the user.

In one embodiment, the pressure detecting mechanism 221 is a three-leg pressure detecting mechanism. Similarly, the three-leg pressure detecting mechanism is located below the bed body 210 and includes three supporting legs for supporting the bed body 210, and each supporting leg is provided with a pressure sensor electrically coupled to the signal processing unit 224.

Figure 6:
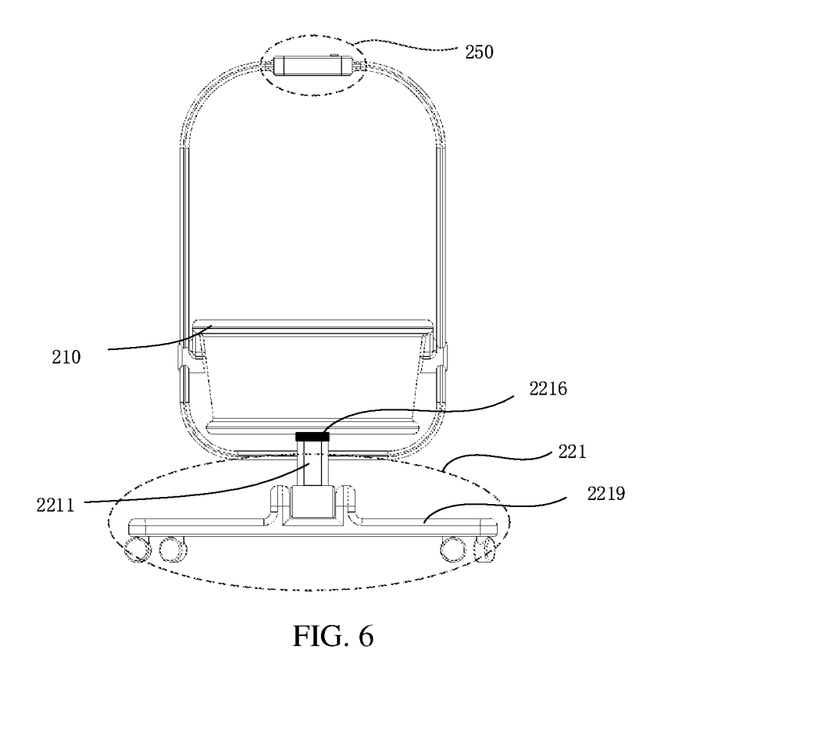
FIG. 6 is a front view of a bed in accordance with another embodiment.

Referring to FIG. 6, in another embodiment, the pressure detecting mechanism 221 is a single-leg pressure detecting mechanism, including a supporting leg 2211. A bracket 2219 is provided below the supporting leg 2211 to enable the supporting leg 2211 to stably support the bed body 210. The supporting leg 2211 is provided with a pressure sensor 2216 electrically coupled to the signal processing unit 224. In this embodiment, the pressure sensor 2216 is located at a junction between the supporting leg 2211 of the single-leg pressure detecting mechanism and the bed body 220. The pressure sensor 2216 is used to detect the pressure difference of the bed body 210 in the loaded state and in the unloaded state, and the pressure variation data thereof during the rest of the user.

It can be understood that the pressure detecting mechanism 221 can also be of other structures, which is not limited thereto.

Referring again to FIG. 3, FIG. 4 and FIG. 5, the first signal emitting unit 222 is used to emit a ranging signal. The first signal emitting unit 222 can each be one or more of a laser emitter, an LED emitter, an infrared emitter, an ultrasonic emitter, an electromagnetic wave emitter, and a millimeter wave emitter. The first signal receiving unit 223 is used to receive the ranging signal. In this embodiment, the first signal emitting unit 222 and the first signal receiving unit 223 are both disposed on the first baffle plate 212. It can be understood that the first signal emitting unit 222 and the first signal receiving unit 223 can be provided on the second baffle plate 213. The ranging signal emitted by the first signal emitting unit 222 is reflected to first signal receiving unit 223 by the second baffle plate 213 to detect the distance between the first baffle plate 212 and the second baffle plate 213 so as to detect the height of the user.

The signal processing unit 224 is electrically coupled to the pressure detecting mechanism 221, the first signal emitting unit 222, and the first signal receiving unit 223, for receiving and processing data from the first signal emitting unit 222 and the first signal receiving unit 223 and the pressure detecting mechanism 221. Specifically, the signal processing unit 224 is used to process to pressure difference of the bed body in the loaded state and in the unloaded state detected by the pressure sensor (the first sensor 2212, the second sensor 2213, the third sensor 2214, and the fourth sensor 2215 of this embodiment) to obtain the weight of the user, and process the pressure variation data during the rest of the user detected by the pressure sensor to sense the rest condition of the user (for example, the breathing condition, the heartbeat condition, and the physical condition of the user during the rest thereof), and process the data from the first signal emitting unit 222 and the first signal receiving unit 223 to obtain the height of the user. The signal processing unit 224 includes a single chip microcomputer, a chip that can implement data processing, and the like.

The monitoring unit 226 is used to receive and monitor the processed signal data generated by the signal processing unit 224. The signal processing unit 224 and the monitoring unit 226 can be coupled via a wired or wireless communication unit for data interaction. The wired communication unit can be a metal wiring. The wireless communication unit includes at least one of a Wi-Fi module, a Bluetooth module, a ZigBee module, a Zwave module, a WLAN module, a GSM module, a 2G module, a 3G module, a 4G module, and a 5G module. During the rest of the user, if the pressure data of the bed body 210 detected by the pressure detecting mechanism 221 fluctuates substantially uniformly, it indicates that the rest condition of the user is stable and the user is in a safe state. The signal processing unit 224 is used to process the pressure variation data detected by the pressure detecting mechanism 221, and transmit a safety signal to the monitoring unit 226 via the wired communication unit or the wireless communication unit. In this case, the monitoring unit 226 is used to monitor the safety signal, and collect the processed signal data. During the rest of the user, if the pressure data of the bed body 210 detected by the pressure detecting mechanism 221 does not change or fluctuates abnormally, it indicates that the rest condition of the user is not stable, a hazardous condition such as apnea, heartbeat pause, abnormal physical activity, and the like may be occur, and the user may be in hazard. The signal processing unit 224 is used to process the pressure variation data detected by the pressure detecting mechanism 221 and transmit a hazardous signal to the monitoring unit 226 via the wired or wireless communication unit. At this time, the monitoring unit 226 is used to detect the hazard signal, collect the processed signal data, and sends an alarm to draw the attention of the caregiver. In this way, the caregiver can take timely measure to prevent adverse consequences.

The display device 250 can be detachably disposed on the bed body 210. The caregiver can place the display device 250 in a convenient viewing position (including but not limited to any position of the bed body 210 or any location of the care setting) as desired. In this embodiment, the display device 250 is disposed on the second side plate 217 of the bed body 210. The display device 250 is electrically coupled to the monitoring device 220. Specifically, the display device 250 is electrically coupled to the signal processing unit 224. Further, the display device 250 is wirelessly electrically coupled to the signal processing unit 224. The signal processing unit 224 is used to process the data from the first signal emitting unit 222, the first signal receiving unit 223, and the pressure detecting mechanism 221, and transmit the processed signal data to the display device 250 for display. In an embodiment, the display device 250 includes a display screen 252, which can be a liquid crystal display screen.

In this embodiment, the bed 200 further includes an voice broadcast unit 260, such as a speaker. The voice broadcast unit 260 is electrically coupled to the signal processing unit 224 for performing voice broadcast on the weight data detected by the signal processing unit 224 according to the pressure difference of the bed body 210 in the loaded state and in the unloaded state detected by the pressure sensor.

In this embodiment, the bed 200 also includes a wireless communication device 270. The wireless communication device 270 includes one or more of a Wi-Fi device, a Bluetooth device, a ZigBee device, a Zwave device, a WLAN device, a GSM device, a 2G device, a 3G device, a 4G device, and a 5G device. The wireless communication device 270 is used to perform data interaction between the signal processing unit 224 and a mobile device or a server via a wireless network. The wireless communication device 270 is electrically coupled to the signal processing unit 224 for transmitting the weight data obtained by signal processing unit 224 according to the pressure difference of the bed body 210 in the loaded state and in the unloaded state detected by the pressure sensor and the breathing condition, the heartbeat condition, and the physical condition data of the user during the rest thereof obtained by the signal processing unit 224 according to the pressure variation data detected by the pressure sensor during the rest of the user to the mobile device or the server (a mobile device such as a mobile phone) via the wireless network signal. The mobile device or the server can store the weight data and the breathing condition, the heartbeat condition, and the physical condition data of the user during the rest, and can display the weight data and the breathing condition, the heartbeat condition, and the physical condition of the user during the rest in a certain way (such as a graph, etc.).

In this embodiment, the bed 200 can further include a power supply device 280 for powering components of the bed 200 that requires to be powered (e.g., the monitoring device 220). The power supply device 280 can be a disposable battery or a chargeable battery. It can be understood that the power supply device 280 can also supply power to the components that requires to be powered after an external alternating current is converted into a direct current.

In this embodiment, the display screen 252 can be provided with operation buttons 254 on both sides thereof. The operation button 254 includes at least one of a lock button, an voice broadcast button, a wireless transmission button, a power button, and a clear button. The lock button is used to prevent a display value of the weight from frequently changing due to shaking of the user when the signal processing unit 224 processes the pressure difference of the bed body 210 in the unloaded state and in the loaded state detected by the pressure detecting mechanism 221. When the user presses the lock button, the display value of the weight is no longer changed. The voice broadcast button is used to provide a choice for the user about whether broadcasting the measuring weight thereof in voice or not. When the voice broadcast button is pressed, the voice broadcast unit broadcasts the measuring weight, otherwise the broadcasting is not performed. The wireless transmission button is used to provide a choice for the user about whether transmitting the measuring results (e.g. the weight data and the breathing condition, the heartbeat condition, and the physical condition of the user during the rest, and the height of the user) to the mobile device or the server via the wireless network. When the wireless transmission button is pressed, the wireless transmission device transmits the measuring results to the mobile device or the server, otherwise the transmission of the measuring results is not performed. The power button is used to supply power to the components of bed body 210 required to be powered (such as the monitoring device 220, the display device 250, the wireless communication device, the voice broadcast device, etc.). When the power button is pressed, the components of bed body 210 required to be powered are powered on, otherwise no power is supplied. In one of the embodiments, a cushion-like article can be placed in the bed body 210 for the comfort of the user. At this time, when the signal processing unit 224 processes the pressure difference of the bed body in a loaded state and in an unloaded state detected by the pressure detecting mechanism 221 to obtain the weight data, and the detected weight may be inaccurate due to the presence of the cushion-like article. The clear button is used to eliminate an effect of the cushion-like article on the detected weight.

When the clear button is pressed, the detected weight no longer contains the weight of the cushion-like article.

In this embodiment, according to afore-described bed 200, the caregiver is not required to detect the weight and height of the user manually, an accuracy of physiological data of the weight and the height of the user can be ensured, and the caregiver can detect the weight and the height of the user while the user plays in the bed 200 without moving the user to a special measuring device to perform the measurements.

Figure 7:
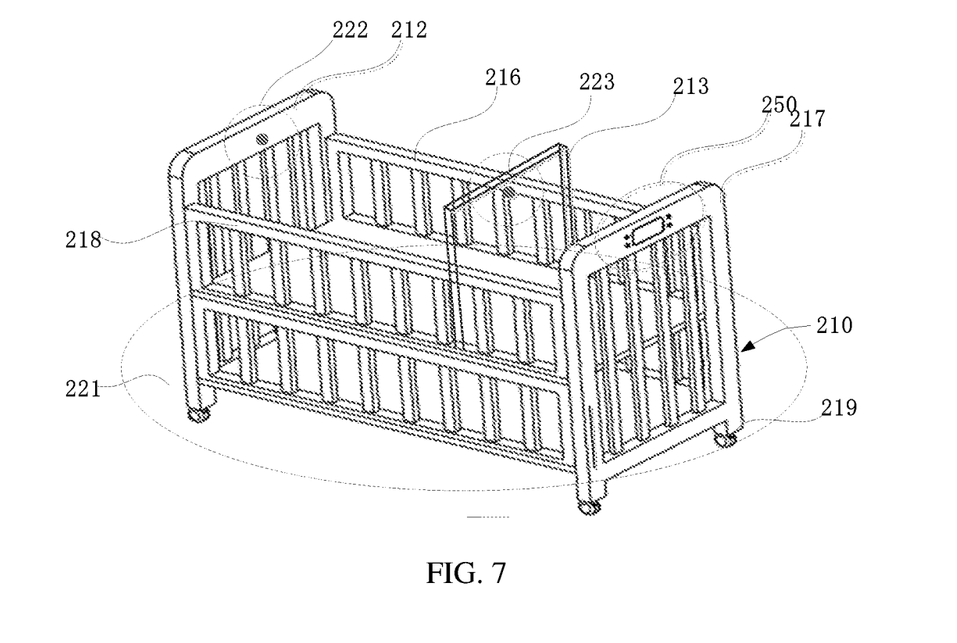
FIG. 7 is a perspective view of a bed in accordance with still another embodiment.
Figure 8:
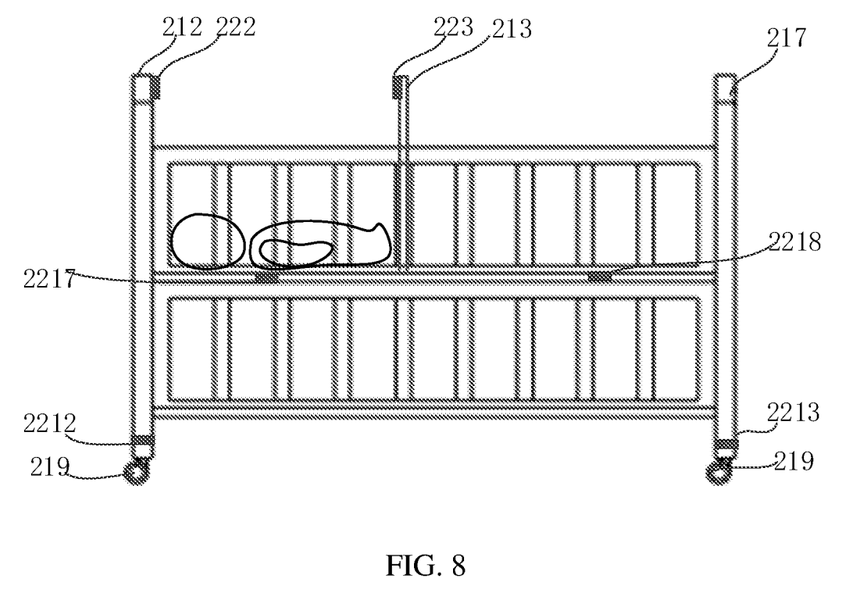
FIG. 8 is a side view of the bed of FIG. 7.

Referring to FIG. 7 and FIG. 8, in another embodiment, one of the first signal emitting unit 222 and the first signal receiving unit 223 is disposed on the first baffle plate 212, the other is disposed on the second baffle plate 213. At this time, the ranging signal emitted by the first signal emitting unit 222 is directly received by the first signal receiving unit 223 without reflection so as to detect the height of the user.

The pressure detecting mechanism of this embodiment is similar to the pressure mechanism shown in FIG. 5, except that the pressure detecting mechanism 221 further includes a fifth sensor 2217 and a sixth sensor 2218 disposed on the backside of the bed plate 211. The fifth sensor 2217 and the sixth sensor 2218 can be pressure sensors or gravity sensors. Similar to the first sensor 2212, the second sensor 2213, the third sensor 2214, and the fourth sensor 2215, the fifth sensor 2217 and the sixth sensor 2218 are used to detect the pressure difference of the bed body 210 in the loaded state and in the unloaded state and the pressure variation data of the bed body 210 during the rest of the user as well. Both of the fifth sensor 2217 and the sixth sensor 2218 are electrically coupled to the signal processing unit 224 to transmit the detected pressure data to the signal processing unit 224. The signal processing unit 224 is used to process the pressure difference of the bed body 210 in the loaded state and in the unloaded state to obtain the weight data of the user, and process the pressure variation data of the bed body 210 during the rest of the user detected by the first sensor 2212, the second sensor 2213, the third sensor 2214, the fourth sensor 2215, the fifth sensor 2217 and the sixth sensor 2218 to sense the rest condition of the user. The signal processing unit is used to transmit the weight data and the breathing condition, the heartbeat condition, and the physical condition data of the user during the rest obtained according to the pressure data detected by the pressure sensor to the display device 250 for display.

It can be understood that in other embodiments, the first sensor 2212, second sensor 2213, third sensor 2214, and the fourth sensor 2215 can be omitted, that is, the sensors only included in the pressure detecting mechanism 221 are the fifth sensor 2217 and the sixth sensor 2218 located on the backside of the bed plate 211.

Figure 9:
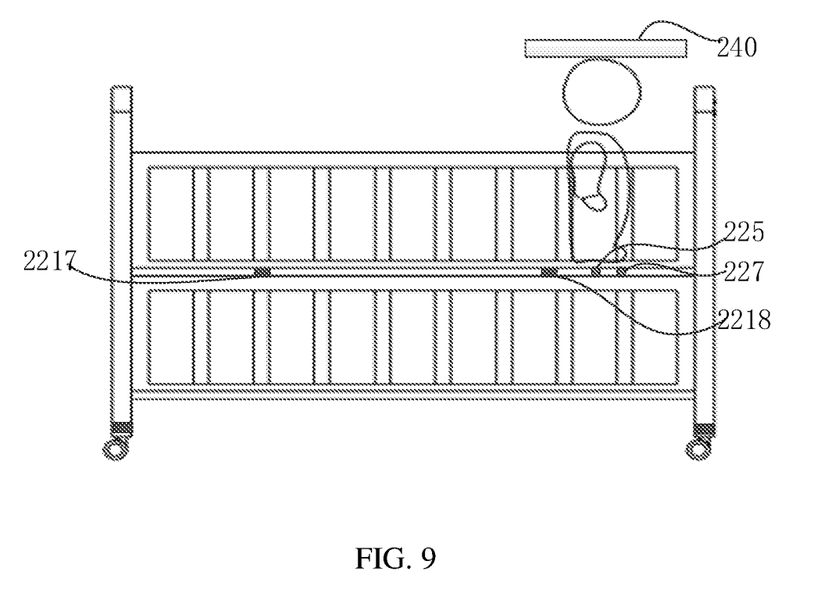
FIG. 9 is a side view of a bed in accordance with yet another embodiment.

Referring to FIG. 9, in still another embodiment, the monitoring device 220 further includes a second signal emitting unit 225 and a second signal receiving unit 227. The second signal emitting unit 225 and the second signal receiving unit 227 are both disposed on the bed plate 211. The second signal emitting unit 225 is used to emit a ranging signal. The second signal receiving unit 227 is used to receive the ranging signal. In this embodiment, the bed body 210 further includes a third baffle plate 240. In this embodiment, the bed plate 211 is used to abut against the sole of the user. The third baffle plate 240 is used to abut against the top heat of the user. The ranging signal emitted by the second signal emitting unit 225 is reflected to the second signal receiving unit 227 by the third baffle plate 240 to detect the height of the user. The third baffle plate 240 is movable relative to the bed plate 211. The third baffle plate 240 can be any objects provided by the user that can reflect the ranging signal, such as a plastic plate, a mobile phone, or the like. The signal processing unit 224 is electrically coupled to the second signal emitting unit 225 and the second signal receiving unit 227, respectively. The signal processing unit 224 is used to process the data from the second signal emitting unit 225 and the second signal receiving unit 227 and transmit the processed data to the display device 250 for display. In this embodiment, when the user stands in the bed 200, the third baffle plate 240 is placed on the top head of the user, and the sole of the user is in contact with the bed plate 211. The third baffle plate 240 is capable of reflecting the ranging signal emitted by the second signal emitting unit 224 to the second signal receiving unit 225 to detect a distance between the bed plate 211 and the third baffle plate 240 so as to detect the height of the user. The height of the user can be accurately detected by processing the data from the second signal emitting unit 225 and the second signal receiving unit 227 through the signal processing unit 224 without manual measurement, which can ensure the accuracy of the height.

It can be understood that in other embodiments, the first signal emitting unit 222 and the first signal receiving unit 223 or the second signal emitting unit 225 and the second signal receiving unit 227 may be omitted, that is, the monitoring device 220 includes only one set of signal emitting unit and signal receiving unit.

The technical features of the above embodiments can be arbitrarily combined. For the sake of brevity of description, all possible combinations of the technical features in the above embodiments are not described. However, as long as there is no collision in the combination of these technical features, it should be considered as the scope described in this specification.

The foregoing implementations are merely specific embodiments of the present disclosure, and are not intended to limit the protection scope of the present disclosure. It should be noted that any variation or replacement readily figured out by persons skilled in the art within the technical scope disclosed in the present disclosure shall all fall into the protection scope of the present disclosure. Therefore, the protection scope of the present disclosure shall be subject to the protection scope of the appended claim.

What is claimed is:

1. A bed comprising:
   a bed body having a space for a user to rest;
   a monitoring device connected to the bed body, the monitoring device comprising a pressure detecting mechanism, a signal processing unit electrically coupled to the pressure detecting mechanism, and a monitoring unit electrically coupled to the signal processing unit;
   wherein the pressure detecting mechanism is configured to detect pressure variations of the bed body, generate pressure data, and transmit the pressure data to the signal processing unit, the signal processing unit is configured to process the pressure data and generate processed signal data, the monitoring unit is configured to monitor the processed signal data, wherein
   the pressure detecting mechanism is a single-leg pressure detecting mechanism, including a single supporting leg,
   the bed body comprises a supporting frame, and the single supporting leg is vertically adjustable and rotatably connected to the supporting frame, a bracket is provided below the single supporting leg to enable the single supporting leg to stably support the bed body, the single supporting leg is provided with a single pressure sensor electrically coupled to the signal processing unit, and the single pressure sensor is proximately located on the single supporting leg at a junction directly between the single supporting leg and the supporting frame.

2. The bed according to claim 1, wherein the pressure data comprises pressure variation data of the bed body generated during rest of the user, the signal processing unit is configured to sense breathing condition, heartbeat condition, and physical condition of the user according to the pressure variation data.

3. The bed according to claim 1, wherein the pressure data comprises a pressure difference of the bed body in a loaded state and in an unload state, the signal processing unit is configured to generate weight data according to the pressure difference.

4. The bed according to claim 1, wherein the pressure detecting mechanism comprises at least one strain gauge pressure sensor or piezoelectric pressure sensor.

5. The bed according to claim 1, wherein the signal processing unit is a single chip microcomputer or a chip capable of implementing data processing.

6. The bed according to claim 1, wherein the monitoring unit is electrically coupled to the signal processing unit via a wired or wireless communication.

7. The bed according to claim 1, wherein the monitoring device is disposed on the supporting frame.

8. The bed according to claim 1, further comprising a display device provided on the bed body, wherein the display device is electrically coupled to the signal processing unit to receive and display data transmitted from the signal processing unit.

9. The bed according to claim 8, wherein the display device is detachably disposed on the bed body.

10. The bed according to claim 1, further comprising a wireless communication device configured to perform data interaction between the signal processing unit and a mobile device or a server via a wireless network.

11. The bed according to claim 1, further comprising a power supply device configured to power the monitoring device.

12. The bed according to claim 1, further comprising a voice broadcast unit electrically coupled to the signal processing unit and is configured to perform voice broadcast on the data transmitted from the signal processing unit.

13. The bed according to claim 1, wherein the monitoring device comprises an emitting unit configured to emit a ranging signal and a receiving unit configured to receive the ranging signal, the signal processing unit is electrically coupled to the emitting unit and the receiving unit, and is configured to process data from the emitting unit and the receiving unit to obtain a height of the user.

14. The bed according to claim 13, wherein the bed body further comprises a first baffle plate abutting against a first portion of the user and a second baffle plate movable relative to the first baffle plate and abutting against a second portion of the user, one of the first portion and the second portion is a top head of the user, and the other is a sole of the user, the emitting unit and the receiving unit are both disposed on the first baffle plate or the second baffle plate, or the emitting unit and the receiving unit are respectively disposed on the first baffle plate and the second baffle plate.

15. The bed according to claim 13, wherein the bed body comprises a bed plate abutting against a sole of the user and a third baffle plate abutting against a top head of the user, the emitting unit and the receiving unit are both disposed on the bed plate, and the third baffle plate is configured to reflect the ranging signal.

16. The bed according to claim 1, wherein the bracket is rotatably connected to the single supporting leg.

17. The bed according to claim 1, wherein an angle between the single supporting leg and the bracket is adjustable.

18. A bed comprising:
a bed body having a space for a user to rest;
a monitoring device connected to the bed body, the monitoring device comprising a pressure detecting mechanism, a signal processing unit electrically coupled to the pressure detecting mechanism, and a monitoring unit electrically coupled to the signal processing unit;
wherein the pressure detecting mechanism is configured to detect pressure variations of the bed body, generate pressure data, and transmit the pressure data to the signal processing unit, the signal processing unit is configured to process the pressure data and generate processed signal data, the monitoring unit is configured to monitor the processed signal data, wherein
the pressure detecting mechanism is a single-leg pressure detecting mechanism, including a single supporting leg;
the bed body comprises a supporting frame, and the single supporting leg is rotatably connected to the supporting frame;
a bracket is provided below the single supporting leg to enable the single supporting leg to stably support the bed body, the bracket being rotatably connected to the single supporting leg;
the single supporting leg is provided with a pressure sensor electrically coupled to the signal processing unit, and the pressure sensor is proximately located on the single supporting leg at a junction between the single supporting leg and the supporting frame.

* * * * *